United States Patent
Ochs et al.

(10) Patent No.: US 8,316,865 B2
(45) Date of Patent: *Nov. 27, 2012

(54) PROCESS FOR WINDING DENTAL TAPE

(75) Inventors: Harold Ochs, Flemington, NJ (US);
Curt Binner, Furlong, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1040 days.

This patent is subject to a terminal disclaimer.

(21) Appl. No.: 12/185,354

(22) Filed: Aug. 4, 2008

(65) Prior Publication Data

US 2010/0024838 A1   Feb. 4, 2010

Related U.S. Application Data

(60) Provisional application No. 61/085,305, filed on Jul. 31, 2008.

(51) Int. Cl.
*A61C 15/00* (2006.01)
(52) U.S. Cl. .................... 132/325; 242/178
(58) Field of Classification Search ............ 132/329, 132/325; 242/169, 159, 178, 174, 176
See application file for complete search history.

(56) References Cited

U.S. PATENT DOCUMENTS

| | | |
|---|---|---|
| 3,771,536 A | 11/1973 | Dragan |
| 3,800,812 A | 4/1974 | Jaffe |
| 3,819,122 A | 6/1974 | Genson |
| 3,838,702 A | 10/1974 | Standish et al. |
| 3,906,757 A | 9/1975 | Arimoto et al. |
| 4,029,113 A | 6/1977 | Guyton |
| 4,068,615 A | 1/1978 | LeNir |
| 4,153,961 A | 5/1979 | Cleveland |
| 4,450,849 A * | 5/1984 | Cerceo et al. ............... 132/321 |
| 4,911,427 A | 3/1990 | Matsumoto et al. |
| 4,911,927 A | 3/1990 | Hill et al. |
| 5,220,932 A | 6/1993 | Blass |
| 5,501,734 A | 3/1996 | Oliphant |
| 5,558,901 A | 9/1996 | Gilligan et al. |
| 5,603,921 A | 2/1997 | Bowen |
| 5,755,243 A | 5/1998 | Roberts et al. |
| 6,035,667 A | 3/2000 | Watabe et al. |
| 6,080,481 A | 6/2000 | Ochs et al. |
| 6,293,287 B1 | 9/2001 | Anglin et al. |
| 6,371,133 B1 | 4/2002 | Gant |

(Continued)

FOREIGN PATENT DOCUMENTS

EP    0 021 677    1/1981

(Continued)

OTHER PUBLICATIONS http://www.plantservices.com/articles/2003/119.html?page=print Maintain the Tension; By: Bob Sarnelli: An AC motor can function as a brake for unwinding applications; Jun. 26, 2008.

(Continued)

*Primary Examiner* — Todd Manahan
*Assistant Examiner* — Brianne Kalach
(74) *Attorney, Agent, or Firm* — Darryl C. Little

(57) ABSTRACT

This present invention relates to a process for winding tape to prevent or reduce telescoping of the tape (e.g., dental tape) as it is wound onto a bobbin spool. Dispensers comprising such bobbins are also discussed herein.

6 Claims, 12 Drawing Sheets

U.S. PATENT DOCUMENTS

| | | | |
|---|---|---|---|
| 6,884,309 B2 | 4/2005 | Schweigert | |
| 7,152,611 B2 | 12/2006 | Brown et al. | |
| 2001/0003587 A1 | 6/2001 | Schiraldi et al. | |
| 2002/0069974 A1* | 6/2002 | Niermann | 156/577 |
| 2003/0143395 A1 | 7/2003 | Koyanagi et al. | |
| 2003/0188762 A1 | 10/2003 | Ochs et al. | |
| 2005/0133654 A1* | 6/2005 | Metzger | 242/422.5 |
| 2007/0068550 A1* | 3/2007 | Zhiwzhinda | 132/321 |
| 2007/0181144 A1 | 8/2007 | Brown et al. | |

FOREIGN PATENT DOCUMENTS

| | | |
|---|---|---|
| WO | 02/59024 | 1/2002 |
| WO | 03/068173 | 8/2003 |

OTHER PUBLICATIONS http://www.enotes.com/how-products-encyclopedia/dental-floss/print ; enotes; Jun. 6, 2008; How Products are Made/Dental Floss.

* cited by examiner

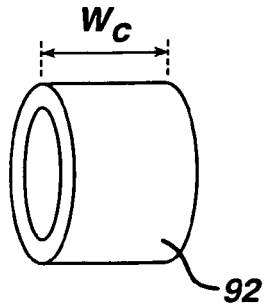
FIG. 21
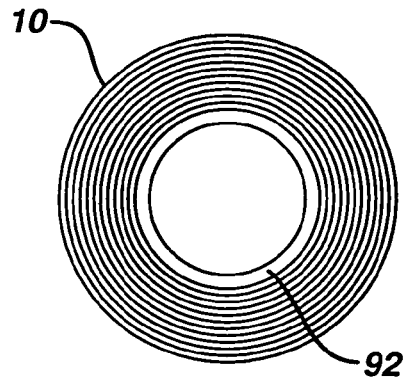
FIG. 22a
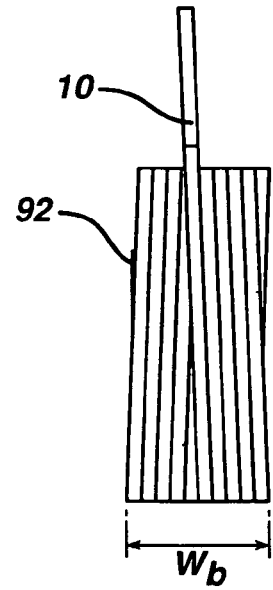
FIG. 22b
FIG. 23a
FIG. 23b
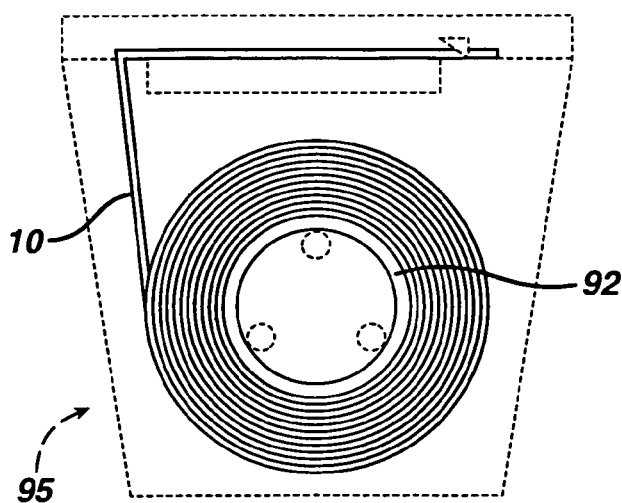
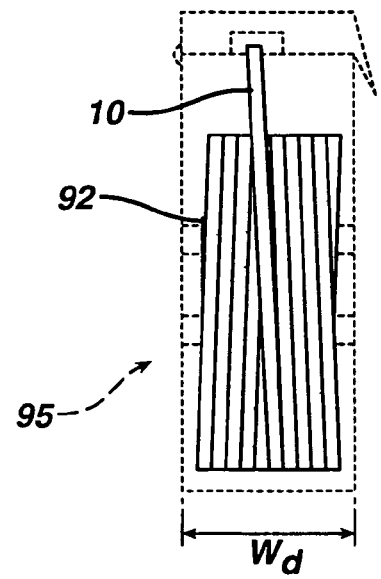

PROCESS FOR WINDING DENTAL TAPE

CROSS-REFERENCE TO RELATED APPLICATION

The present application is a utility application claiming the benefit of the earlier filing date of U.S. patent application 61/085,305, filed Jul. 31, 2008, the entirety of which applications are hereby incorporated as if fully set forth herein

FIELD OF THE INVENTION

This present invention relates to a process for winding tape to prevent or reduce telescoping of the tape (e.g., dental tape) as it is wound onto a bobbin spool. Dispensers comprising such bobbins are also discussed herein.

BACKGROUND OF THE INVENTION

Dental floss has been in use for more than 100 years for removing plaque and entrapped food particles from between teeth, as well as providing a clean feeling in the mouth. The reduction of bacteria in the mouth is important because bacteria can cause cavities and gum disease. Dental flossing has been shown to remove bacteria in the interproximal as well as in the subgingival regions of the mouth.

The original floss consisted of twisted silk placed in a jar. Since then, many improvements have been made to dental floss to make flossing more convenient and less problematic. Most improvements have been aimed at solving the negative aspects of flossing. These include reducing fraying and breakage, providing easier insertion between teeth and providing a softer, more gum and hand friendly floss. Nylon, a high tenacity fray-resistant yarn, was first used to replace the silk, providing more fray resistance. The addition of wax to twisted multifilament yarn helped anchor fibers together, while providing a lubricious coating for easier insertion. Low friction monofilament PTFE yarn coated with wax provides good ease of insertion, depending upon the thickness and lack of twists or folds, as well as improved fray resistance. Unfortunately, PTFE monofilaments do not clean well, nor do they easily remove food particles from the space between teeth due to the low coefficient of friction of PTFE.

Further improvements to flosses were made by providing monofilament tapes made of elastomeric materials which neck down when passing into the interdental space and then expand upon relieving tension. Monofilament dental tapes made of elastomeric materials have been found to be difficult to process. One problem encountered with elastomeric dental tape products of the type described is called "telescoping." In a roll of dental tape or bobbin of dental tape which suffers from telescoping, successive layers of the tape wound upon the core are displaced axially. Thus, the bobbin of tape takes on a generally conical shape rather than the cylindrical shape of a tape product not suffering from telescoping. A bobbin of dental tape suffering from a severe case of telescoping often cannot be mounted on or into a dispenser.

Telescoping may be the result of the elastomeric properties of the material comprising the dental tape. Bobbins of elastomeric tape formed under high tension from supply rolls are more likely to suffer telescoping since the increased tension increases the stress on the bobbin. High tension during the bobbin forming process generally stems from high tape tension during the supply roll forming process. High tension during the supply roll forming process can result from non-uniformities in the velocity or tension (i.e., accelerations and decelerations) on the tape as it is being processed or from additional tape processing such as from the coating process. During the coating process the tape is typically stretched and relaxed as it moves through coating apparatuses, thus further contributing to increased tension. Without being limited by theory, the present inventers have discovered that by lowering the tension at which the supply rolls are formed, the tension is proportionately lowered during the bobbin forming process.

There is a continuing need for coated monofilament tapes that do not have telescoping issues, as well as methods of processing these dental tapes.

SUMMARY OF THE INVENTION

This present invention relates to a process for winding tape to prevent or reduce telescoping of the tape as it is wound onto a bobbin spool. Dispensers comprising such bobbins are also discussed herein.

In one embodiment, the present invention relates to a process for winding elastomeric tape, comprising the steps of:
a. providing a powered rewinding mechanism for rewinding the tape onto a take-up spool having a core, the spool having a longitudinal axis and a constant circumference C along the length of the longitudinal axis, the rewinding mechanism comprising;
  i. a traverse barrel cam providing a cam advance and
  ii. pulleys in driving communication with and sequentially ordered from the take-up spool to the traverse barrel cam such that the product of the pulley ratios is a Ratio A, where;

Ratio $A = P_1/P_2 \times P_3/P_4 \times P_{z-1}/P_z$ where Z is the number of pulleys used to drivingly connect the traverse barrel cam to the take-up spool and $P_1$ to $P_z$ are the sizes of the pulleys as sequentially ordered from the take-up spool to the traverse barrel cam, the traverse barrel cam and the pulley sizes selected such that the product of the cam advance and Ratio A when divided by the circumference C produces a Ratio B, where Ratio $B = $ (cam advance $\times$ Ratio $A$)/Circumference $C$ and where Ratio B provides a Helix Angle $\theta$ of from about 3.5 degrees to about 5 degrees, when determined by formula:

$\sin^{-1}$(Helix Angle $\theta$) = Ratio $B$ b. optionally, providing a sensing mechanism coupled to the powered unwinding mechanism for maintaining the speed of the tape such that the tension is less than 250 grams-force just prior to the rewinding of the tape onto the take-up spool; and
c. winding no more than 6 pounds of the elastomeric tape onto the take-up spool.

In another embodiment, the present invention relates to a process for coating and winding elastomeric tape, comprising the steps of:
a. providing a powered unwinding mechanism for unwinding a spool of elastomeric tape having a first side and a second side, the first side being opposite the second side;
b. providing a line speed for the tape of greater than about 1000 feet per minute;
c. providing a die coating mechanism comprising a coating die adapted to receive or orientate the elastomeric tape such that the first and second sides are at a vertical orientation and comprising coating outlet ports for delivering coating to the first and second sides of the elastomeric tape;

d. providing a powered rewinding mechanism for rewinding the tape onto a take-up spool having a core, the spool having a longitudinal axis and a constant circumference C along the length of the longitudinal axis, the rewinding mechanism comprising;
  i. a traverse barrel cam providing a cam advance and
  ii. pulleys in driving communication with and sequentially ordered from the take-up spool to the traverse barrel cam such that the product of the pulley ratios is a Ratio A, where;

Ratio $A = P_1/P_2 \times P_3/P_4 \times P_{z-1}/P_z$ where Z is the number of pulleys used to drivingly connect the traverse barrel cam to the take-up spool and $P_1$ to $P_z$ are the sizes of the pulleys as sequentially ordered from the take-up spool to the traverse barrel cam, the traverse barrel cam and the pulley sizes selected such that the product of the cam advance and Ratio A when divided by the circumference C produces a Ratio B, where Ratio $B$=(cam advance×Ratio $A$)/Circumference $C$ and where Ratio B provides a Helix Angle θ of from about 3.5 degrees to about 5 degrees, when determined by formula:

$\sin^{-1}$(Helix Angle θ)=Ratio $B$ e. optionally, providing a sensing mechanism coupled to the powered unwinding mechanism for maintaining the speed of the tape such that the tension is less than 250 grams-force just prior to the rewinding of the tape onto the take-up spool; and
f. winding no more than 6 pounds of the elastomeric tape onto the take-up spool.

In a further embodiment, the present invention relates to a bobbin of elastomeric tape, comprising:
  a. a spool having a width; and
  b. an elastomeric yarn wound onto the spool such that it forms a width, wherein the percent at which the width formed by the elastomeric yarn exceeds the width of the spool by no more than 10 percent of the width of the spool.

In a still further embodiment, the present invention relates to a dental tape dispenser comprising
  a. a housing;
  b. a bobbin movably connected within the housing, the bobbin comprising:
    i. a spool having a width; and
    ii. an elastomeric yarn wound onto the spool such that it forms a width,
  wherein the percent at the which width formed by the elastomeric yarn exceeds the width of the spool by no more than 10 percent of the width of the spool.

BRIEF DESCRIPTION OF THE DRAWINGS

FIG. 21 is a perspective view of a bobbin spool core.

FIG. 22a is right side elevational view of a tape bobbin with tape wound around the bobbin spool core.

FIG. 22b is a front elevational view of a tape bobbin with tape wound around the bobbin spool core showing the bobbin spool core width relative to the bobbin tape width.

FIG. 23a right side elevational view of a tape bobbin movably positioned within a dispenser (phantom lined).

FIG. 23b is a front elevational view of a tape bobbin movably positioned within a dispenser (phantom lined) depicting the relative bobbin spool core, bobbin tape and dispenser widths.

DETAILED DESCRIPTION OF THE INVENTION

Figure 1:
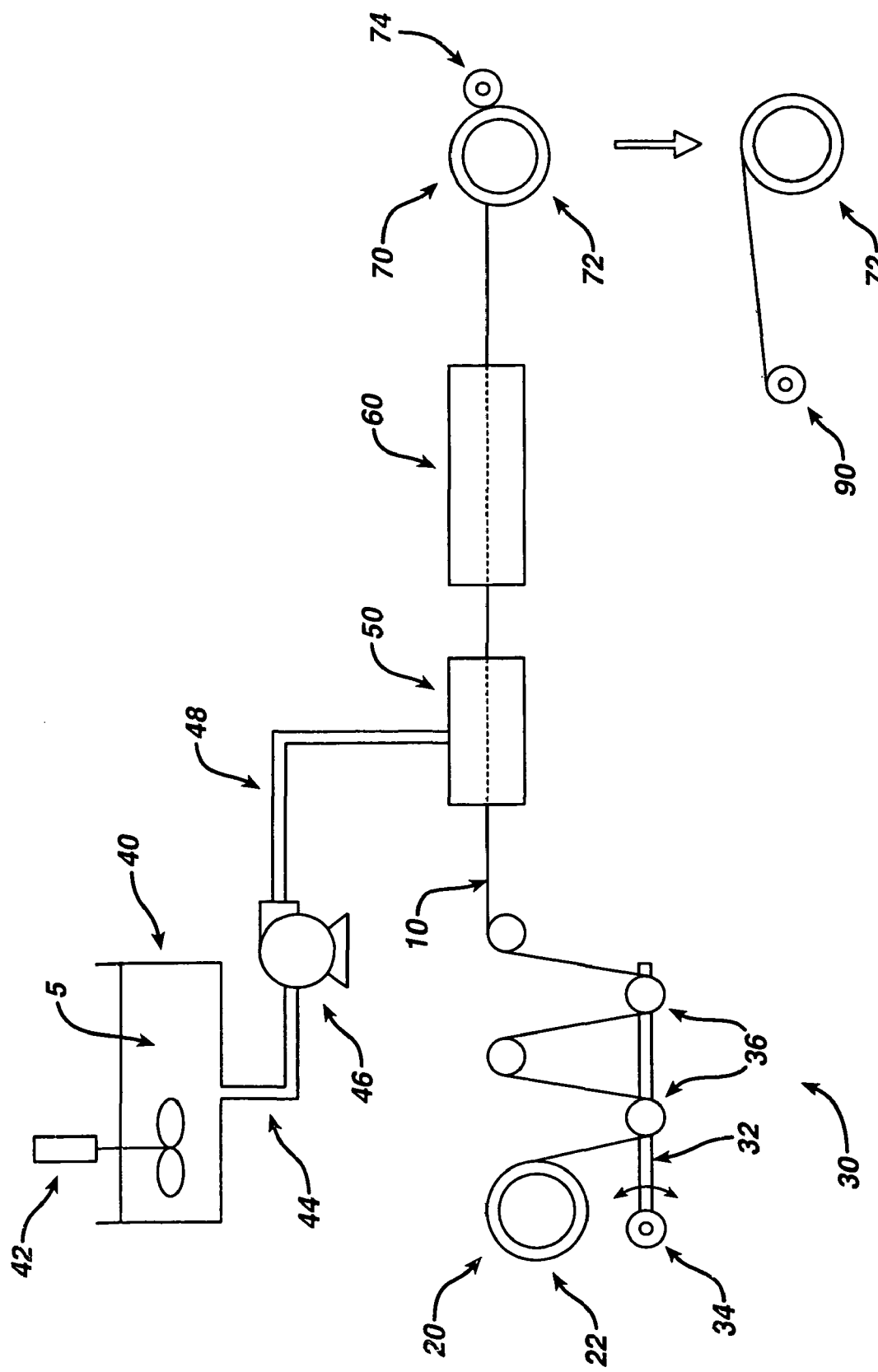
FIG. 1 is a schematic illustration of one embodiment of the manufacturing line for unwinding, coating and rewinding the dental tape of the present invention.

Dental tapes of the present invention are in the form of a single monofilament. As used herein, the terms "tape", "yarn"

and floss are interchangeable. The tapes may be, for example, circular or rectangular in cross-section with a smooth surface. A monofilament tape in rectangular form typically has a width ranging from about 1.0 mm to about 2.0 mm, a thickness ranging from about 0.03 mm to about 0.09 mm, and a denier ranging from about 600 to about 1800. In a specific example, a rectangular monofilament substrate has a width of about 1.8 mm, a thickness of about 0.05 mm, and a denier of about 940.

Alternatively, the monofilament dental tape of the present invention maybe a high surface area tape or have a substantially higher surface area than the tapes with smooth or non-textured surfaces discussed above. A high surface area tape or a tape of a substantially higher surface area is defined as a tape in which the surface area is 15% (or about 15%), or optionally 20% (or about 20%), or optionally 25% (or about 25%) greater than the surface area of a flat, smooth or non-textured tape of equivalent surface dimensions of length, width and height. By "non-textured", it is meant that the surface has no raised and depressed areas that (1) are capable of being felt by a human hand and/or (2) form contours that are discernible by a human eye without magnification. For example, a millimeter of monofilament tape A of 1.8 mm wide and 0.05 mm thick has a surface area of 3.7 $mm^2$. A millimeter of tape B of the present invention would have the same monofilament tape dimensions of 1.8 mm wide and 0.05 mm thick, but also has surface protrusions and/or indentations (e.g., ribs) such that tape B has a higher surface area than tape A. If there are 11 ribs added onto each side of tape A and each rib is 0.04 mm high and 0.04 mm wide, the surface area of the new tape (i.e., tape B) is increased to 5.46 $mm^2$ or 48%. These tapes have the capacity to anchor a surface coating that may be required to provide the dental tape with functions other than those of interdental cleaning, such as flavoring, bactericide, abrasive, sensate, sialagogue, coloring, aromatizing, therapeutical, etc., in relation to the same characteristics of smooth monofilament tapes.

In one embodiment, dental tapes may comprise a core body having a first external face and a second external face opposite the first external face, wherein at least one of the first and second external faces comprises a plurality of indentations protruding into the core body of the dental tape. The indentations may be provided in from about 5% to about 95% of the total area of the at least one of the first and second external faces, and may have a depth within the core body, in relation to the at least one of the first and second external faces comprising the plurality of indentations, corresponding to from about 0.1% to about 50% of the thickness of the core body, taken transversally to the at least one of the first and second external faces comprising the plurality of indentations. Tapes such as these are disclosed in U.S. patent application Ser. No. 12/026,839, which is incorporated by reference herein.

In another embodiment, monofilament dental tapes according to the present invention may comprise a core body having first and second opposing cleaning surfaces, where at least one of the cleaning surfaces comprise a plurality of ribs disposed along the length thereof. As used herein, the term "rib" means a structural element integral with and protruding from the core body of the dental tape, which element has a configuration and dimension effective to provide for removal of plaque and/or food debris from interdental spaces of a mammal. Ribs may protrude substantially perpendicularly from the core body of the dental tape or at an angle. Tapes such as these are disclosed in U.S. patent application Ser. No. 11/937,025, which is incorporated by reference herein.

In certain embodiments, the tape is made using an elastomeric material. Elastomeric materials provide a high degree of compressibility when extruded in the cross-sectional configurations of this invention, allowing it to slip through the tight spaces between teeth. Once in the cavity between teeth and into the interdental space, the tape substantially recovers from compression, providing cleaning surfaces that act as scrapers to remove plaque and food particles from between the teeth. Elastomeric materials that may be used to form the multi-ribbed monofilament dental tape of the present invention include, but are not limited to polyamide-polyether block copolymers sold under the tradename PEBAX (Ato Chimie, Hauts-de-Seine France), such as PEBAX 7033, 5533 MX1205, 4033, 3533, and 2533; polyester-polyether block copolymers and polyester-polyester block copolymers sold under the tradename HYTREL (E. I. du Pont de Nemours & Co., Wilmington, Del.), such as HYTREL 7246, 5556, and 4056; aliphatic thermoplastic polyurethane elastomers sold under the tradename TECOFLEX (Lubrizol Advanced Materials, Inc., Cleveland Ohio); aromatic thermoplastic polyurethane elastomers sold under the tradename PELLETHANE (Dow Chemical Co., Midland, Mich.); and thermoplastic polyolefin elastomer sold under the name MULTI-FLEX (Dow Chemical Co., Midland, Mich.). A more detailed discussion regarding such elastomeric materials and their use in manufacturing dental tape can be found in U.S. Pat. No. 6,591,844 to Barlow et al. filed Aug. 23, 2001 and U.S. Pat. No. 6,029,678 to Tsao et al. filed Jan. 21, 1998, both of which are herein incorporated by reference in their entirety.

The dental tape of the invention may also be made from a substrate referred to as a pseudo-monofilament yarn. Pseudo-monofilament tapes are made by extruding bicomponent fibers typically having a core of one polymer and a sheath of a different polymer, then either partially or totally melting the sheaths of the fibers to bond or fuse the fibers, resulting in a monofilament appearance and feel.

In preferred embodiments of the present invention, coatings can be placed on the first and/or second cleaning surface of the dental tape. Coating compositions for use in the present invention must reliably adhere to the surface of elastomeric monofilament dental tape as well as non-elastomeric tapes, whether the tape is a monofilament or pseudo-monofilament yarn. By "reliably" as used herein is meant that the coating composition must have sufficient adherence to keep about 95%, optionally about 90%, optionally about 85% of the coating on the surface of the tape during coating, winding, shipping and unwinding of the tape. By "pseudo-monofilament" is meant tapes made by extruding multi- and/or bi-component fibers typically comprising a core of one polymer and a sheath of a different polymer and, then, either partially or totally melting the sheaths of the fibers to bond and/or fuse the fibers resulting in a monofilament appearance and/or feel.

Suitable insoluble coatings include, but are not limited to, microcrystalline wax, beeswax, paraffin waxes, low molecular weight polyethylenes, silicone oils, essential oils, and mineral oil. Typically, the insoluble wax coatings have melting temperatures ranging from about 25° C. to about 100° C., optionally from about 35° C. to about 80° C. The waxes may be combined with water insoluble colorants that are FD&C approved for use in the mouth. Suitable colorants include, but are not limited to, synthetically derived colorants such as FD&C Blue #1 Lake, FD&C Blue #2 Lake, FD&C Red #40 Lake, Erythrosin Lake, Amaranth Lake, Ponceau 4R Lake, Carmoisosine Lake, Carmine Lake and colorants generated by converting a naturally derived dye to an aluminum or calcium based salt. Natural colorants such as titanium dioxide and the like may also be used.

The coating composition applied to the dental tape may be a soluble coating, i.e., the coating is such that it tends to dissolve or disperse in saliva present in the oral cavity. Such soluble coatings include soluble waxes or the like, which include, but are not limited to, low molecular weight polyethylene glycols ("PEGs"), such as PEG 1000 and PEG 1450. Combinations of higher molecular weight PEGs and lower molecular weight PEGs, such as a mixture of PEG 3350 and PEG 1000 may be used. Blends of liquid PEG's with high molecular weight PEG's may also be used.

Other coatings include meltable surfactants such as Polyoxamer 407; sialagogues; olfactory stimulants; sensates; essential oils; actives, such as fluoride; cetyl pyridinim chloride (CPC); tetra sodium pyrophosphate; whitening agents such as calcium peroxide, hydrogen peroxide, carbamide peroxide and other peroxide compounds capable of generating hydrogen peroxide in-situ; antimicrobials; anti-virals and mixtures thereof.

Such ingredients may be employed as solids, liquids, particles, gels, or the like, and may be encapsulated in conventional polymeric materials by conventional encapsulation techniques to form encapsulated materials having a polymeric shell and a core comprising the ingredient in one of the noted forms, as the case may be. Such ingredients also may be applied directly to the dental tapes of the present invention without the need for a coating carrier, where appropriate.

A coating comprising an insoluble wax may be applied, wherein the coating contains encapsulated components such as spray dried flavors, essential oils, or other ingredients protected and released from soluble spheres within the insoluble wax, or a soluble coating may be applied directly to the yarn or over the insoluble coating. The soluble coating may contain ingredients that are placed directly in the wax or through the use of spray dried or other encapsulation technologies commonly practiced within the art.

In certain embodiments, two insoluble coatings are applied to the fiber substrate. In these embodiments, the second coating composition should have a lower melting point than the first coating composition.

A soluble coating can be used by itself or as a second coating over an insoluble coating. One or both coatings can contain colorants, flavors, sweeteners, abrasives, anti-tartar agents, actives, such as fluoride salts, and like additives known in the art.

Additional components can be added to coatings for various benefits. These include flavor systems, such as spray dried flavors, flavor enhancers, and sweeteners, such as sodium saccharin. The amount of flavor added typically ranges from 10 percent to 25 percent, based on the total weight of the coating composition. The amount of sweetener typically ranges from 0.1 percent to 1 percent, based on the total weight is of the coating composition.

Other components can be added to coatings to assist in cleaning the teeth. These include actives including abrasives such as silica or di-calcium phosphate, and anti-tartar agents such as tetra-sodium-pyrophosphate. Where two coatings are used, actives are usually added in the second soluble coating to guarantee that a high percentage of the active will be released from the floss during use.

In formulating a coating, it is desirable to limit the amount of solid additives in the coating composition below about 30% by weight. Coating a dental tape with a coating composition having a solid additive content above this amount may cause difficulty in achieving uniformity of coating and reduce the ability of the coating to adhere to the tape surface. Coatings containing high amounts of solid additives may tend to flake off during processing and during use of the final product.

The dental tape coating may be anhydrous or hydrous. When the coating is hydrous, the water is evaporated upon drying.

The coating may be applied as an add-on typically ranging from about 10 percent to about 60 percent, optionally from about 20 percent to about 50 percent, based on the weight of the fiber substrate.

In certain embodiments, the dental tape is manufactured using equipment and processes capable of doing the following:
1. Feeding monofilament tapes to the coating die at a controlled speed and tension so as to avoid telescoping issues,
2. Pumping the coating composition in a uniform fashion into an application die,
3. Uniformly and simultaneously applying the coating composition to both sides of the dental tape, and
4. Providing a sufficient period of time during which the coating composition is substantially undisturbed on the dental tape until it is solidified intact.

By "uniform" or "substantially uniform," it is meant that, when manually (without the aid of measuring instrumentation) or visually (without the need for magnifying devices beyond corrective eyewear) inspected, the coating should have an even (or relatively [or, substantially] even) thickness and be free from (or sufficiently [or substantially] free from) defects (such as pinholes or voids) in the coated area. The above-mentioned process for manufacturing the monofilament dental tape of the invention is illustrated in FIG. 1. In the first step, the coating composition 5, typically a wax, is liquefied if necessary, as by heating, in a mix tank 40. A high sheer mixer 42, such as a Rotostat High Sheer Mixer Model #XPBL, made by Admix, can be used to keep coating composition 5 homogeneous. Typically, a Rotosolver head blade is used in the high sheer mixer 42 and is operated at, e.g., 1700 rpm.

The coating composition is then allowed to flow from mix tank 40, via a first pipe 44 into a positive displacement pump 46 which, when driven at a given speed, delivers a constant amount of coating, via a second pipe 48, to a coating die 50. The positive displacement pump can be a vane type positive displacement pumps, piston pumps, or similar type pumps. In certain embodiments, a Kerr piston pump, supplied by Kerr Corp. Sulfur Okla., is used. Piston pumps, generally, facilitate the evenness and uniformity of coatings where the coating composition 5 contains solid particulates such as abrasives. In certain embodiments, positive displacement pumps are used since the passage bores, pipes, channels or outlets used in such embodiments to deliver coating composition 5 are generally positioned or oriented such that the directional path or track of the passage bores, pipes, channels or outlets points upwardly and toward or horizontally level with and toward the position of the dental tape 10 to be coated such that gravity has no effect or minimal effect on the flow of the coating composition from mix tank 40 onto the dental tape 10.

In certain embodiments, the dental tape 10 is simultaneously fed and pulled through the process by a combination of a powered unwinding system 20 and a floss rewinding system 70. The dental tape 10 is fed or unwound at a low tension and, in certain embodiments, pulled perpendicularly from feed spool 22 across or through sensing arm assembly 30. Sensing arm assembly 30 is provided for monitoring the tension of the dental tape 10 as it enters coating die 50. In certain embodiments, the sensing arm assembly 30 has an arm 32, a pivot point 34, and rollers 36 over which the dental tape 10 passes. Sensing arm assembly 30 is used to maintain a substantially constant low feeding or unwinding tension on dental tape 10 by adjusting the speed of power unwinding system 20 as it is simultaneously fed and pulled into the coating process system. In certain embodiments, where the dental tape passes through the coating process at line speed rates greater than about 1000 feet per minute (fpm), or optionally from about 1500 fpm to about 2500 fpm, or optionally from about 2000 fpm, the constant low unwinding tension is generally maintained at from about 50 grams-force to about 100, optionally at from about 60 grams-force to about 100 grams-force, for dental tape 10 having denier of about 400 to about 1200.

After coating, dental tape 10 is collected on a take-up spool 72. The speed at which take-up spool 72 operates is controlled by an electronic controller system. The controller may be a computer, a programmable logic controller or similar device. In the embodiment shown in FIG. 1, a speed sensing roll 74 rides on surface of the tape on take-up spool 72. Speed sensing roll 74 generates a signal which is fed to an electronic controller, such as a Fenner M-drive. The controller controls the voltage of motor 80 (shown in FIG. 2) which drives the speed of take-up spool 72. The use of the signal generated by speed sensing roll 74 in controlling the speed of take-up spool 72 helps to maintain a constant speed or velocity of the dental tape 10 through the coating process, controlling and maintaining the tension on dental tape 10 to less than 250 or (about 250) grams-force. The electronic controller also controls the speed of positive displacement pump 46. Thus the velocity of dental tape 10 is maintained while a constant amount of coating composition 5 is pumped into the coating die 50.

Figure 8:
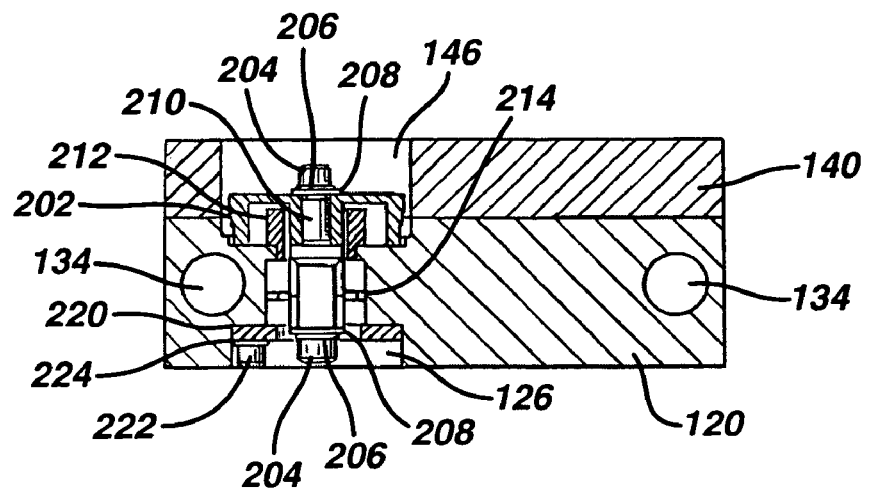
FIG. 8 is a cross-sectional view of a roller assembly of a coating die according to the exemplary embodiment of FIG. 6 along the plane 8-8.

In certain embodiments, not shown in FIG. 1, the coating die 50 contains at least two rollers around which dental tape 10 has at least some wrap. In certain embodiments, the number of rollers can range from 2, optionally 3, optionally 4 or greater rollers, or optionally 2 to 7 rollers or, optionally, from 3 to 5 rollers. Generally, dental tape 10 wraps around the rollers at from about 90° to about 270°. The rollers assist in applying coating composition 5 to dental tape 10. Downstream of the rollers there is typically a slot die region where coating composition 5 is smoothed onto the surface of dental tape 10. In certain embodiments, the slot die is in the form of a groove having parallel sides or walls, the groove, optionally, having a radius at its bottom for guiding the dental tape into a slot. In certain embodiments, the slot is sized such that excess coating is removed from dental tape 10 as it passes through the die (as shown at FIG. 8) while, at the same time, minimizing any additional tension on dental tape 10 caused by the slot die as the tape 10 passes through the die. As will be apparent to those skilled in the art, the dimensions of the groove and slot will depend upon such factors as the denier and type of dental tape 10 and the amount of coating composition 5 being applied thereto.

In certain embodiments, a coating die useful in coating high surface area dental tapes may be used. Such coating dies are adapted to receive or orientate the dental tape 10 such that the planar surface of the dental tape 10 is in a vertical position (or oriented such that the width dimension of dental tape 10 is perpendicular to horizontal plane of the coating die base) (as described in FIG. 5). Without being limited by theory, it is believed that such a vertical orientation better facilitates evenness and uniformity of the coating across the sides of the planar surface of the dental tape 10 than does movement of a horizontally oriented tape through the coating die.

Figure 3:
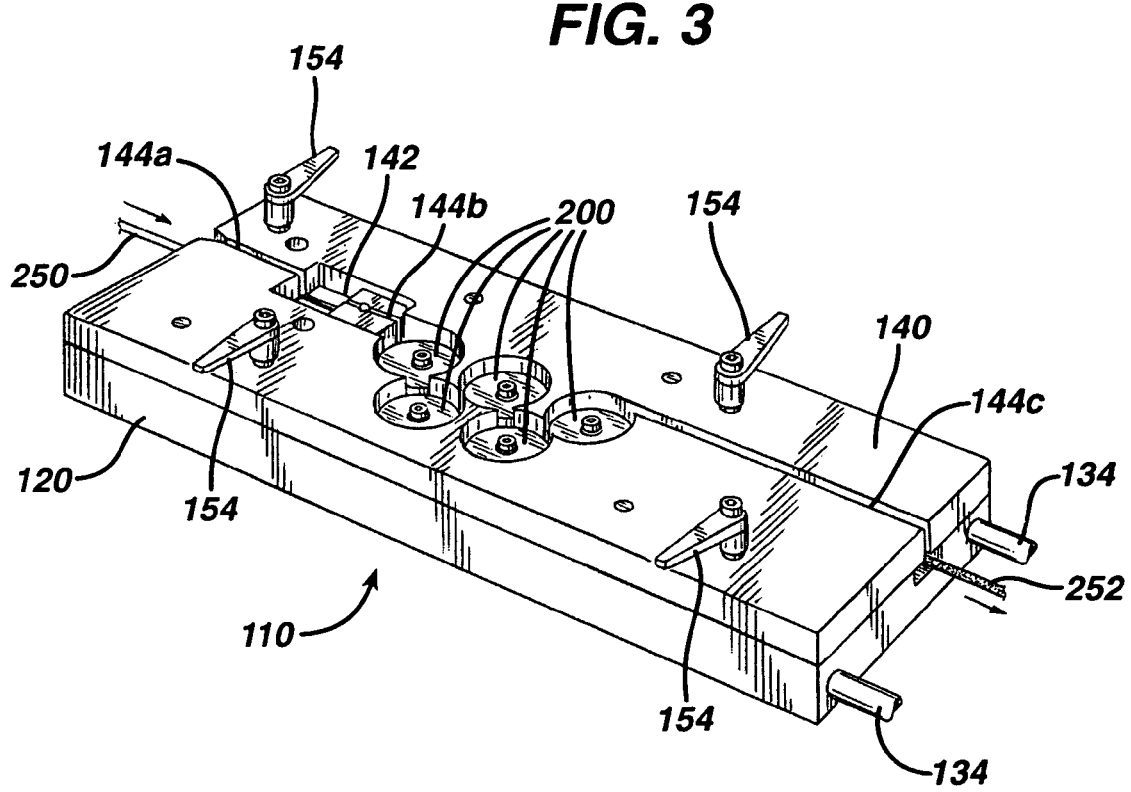
FIG. 3 is a perspective view of a roller coating die according to an exemplary embodiment of the present invention.

One embodiment of a coating die useful in coating high surface area dental tapes is shown in FIGS. 3 to 18. FIG. 3 is a perspective view of roller coating die 110, including roller die base 120 and cover plate 140. Uncoated dental tape 250 enters coating die 110 such that the planar surface of the dental tape 250 is vertically oriented or oriented such that its width dimension of dental tape 250 is perpendicular to roller die base 120. Dental tape 250 traverses vertically along cover plate die slot 144 and roller assemblies 200, and exits as vertically oriented, coated dental tape 252. FIG. 3 shows three sections of cover plate slot 144. Slot 144a traverses from the die entrance to entrance block window 142. Slot 144b traverses from entrance block window 142 to roller assemblies 200. Slot 144c traverses from roller assemblies 200 to the die exit.

Optionally, heaters can be incorporated into or associated with the coating dies of the present invention. The heaters are used to provide temperatures sufficient to keep the coating composition, typically a waxy material, flowable or in a liquid state. Such temperatures typically range from 180° F. to about 200° F. FIG. 3 shows an exemplary embodiment of the present invention having two cartridge heaters 134, which can be used for heating the rollers and/or other components of coating die 50.

Figure 4:
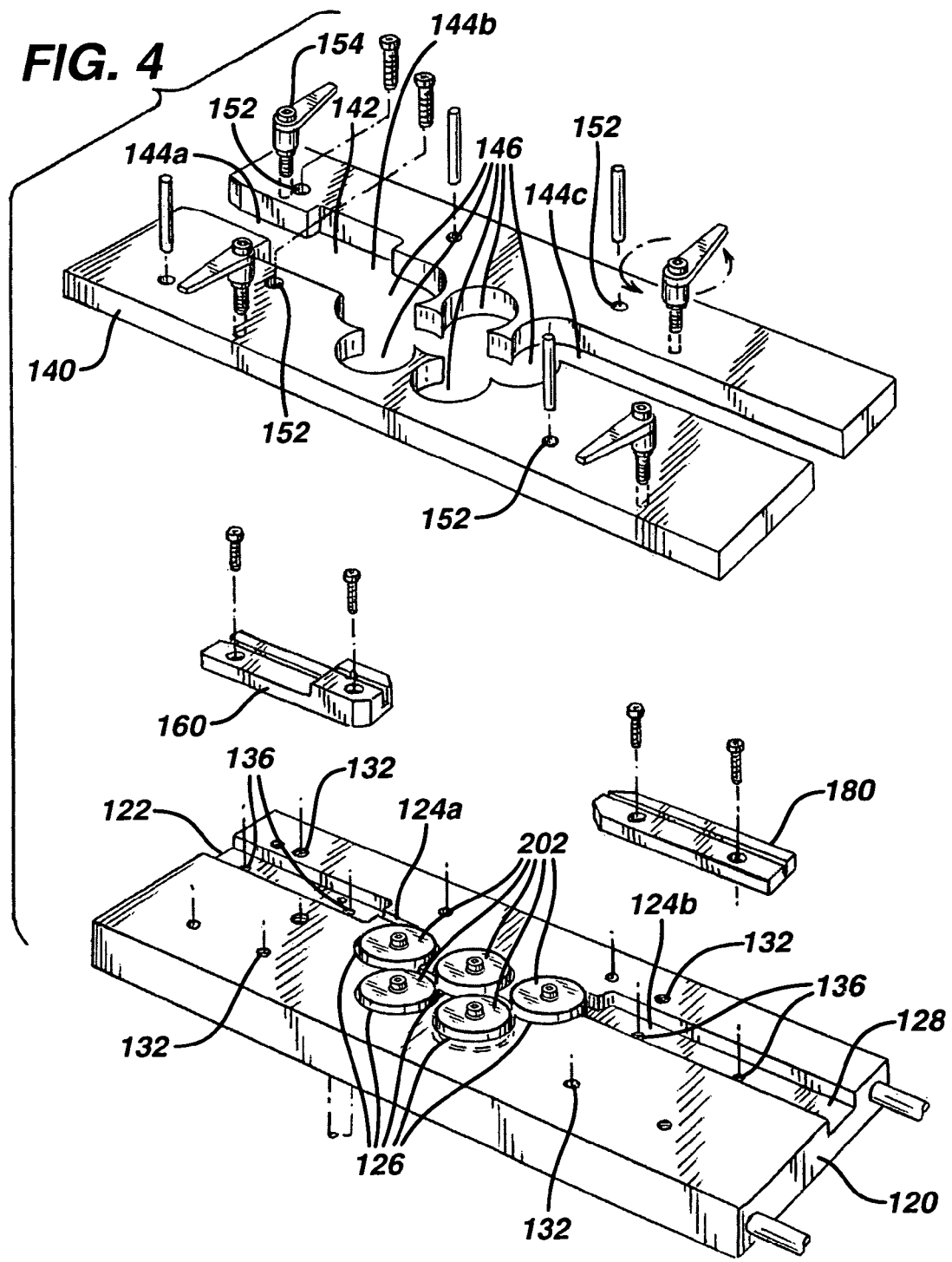
FIG. 4 is an exploded perspective view of a roller coating die according to an exemplary embodiment of the present invention.

FIG. 4 is an exploded perspective view of roller coating die 110, showing more details of roller die base 120 and cover plate 140. In addition to the three sections of cover plate slot 144 and cover plate window 142, five roller wheel windows 146, and four cover plate attachment holes 152 are shown on cover plate 140. Cover plate attachment holes 152 align with roller die base attachment holes 132. Roller die base attachment holes 132 are threaded. Threaded handle 154 is used to hold together roller die base 120 and cover plate 140.

Roller die base 120 includes entrance block recess 122, roller assembly recesses 126, exit block recess 128, roller die base attachment holes 132, and entrance and exit block attachment holes 136. FIG. 4 shows two sections of base slot 124. Base slot 124a traverses from entrance block recess 122 to roller assembly recesses 126. Slot 124b traverses from roller assembly recesses 126 to exit block recess 128. Entrance and exit block attachment holes 136 are threaded.

FIG. 4 also shows entrance block 160, exit block 180, as well as five rollers 202. Entrance block 160 and exit block 180 are positioned between roller die base 120 and cover plate 140, and are used to guide uncoated dental tape 250 from the entrance of coating die 110 to roller assemblies 200, and coated dental tape 252 from roller assemblies 200 to the exit of coating die 110.

Figure 5:
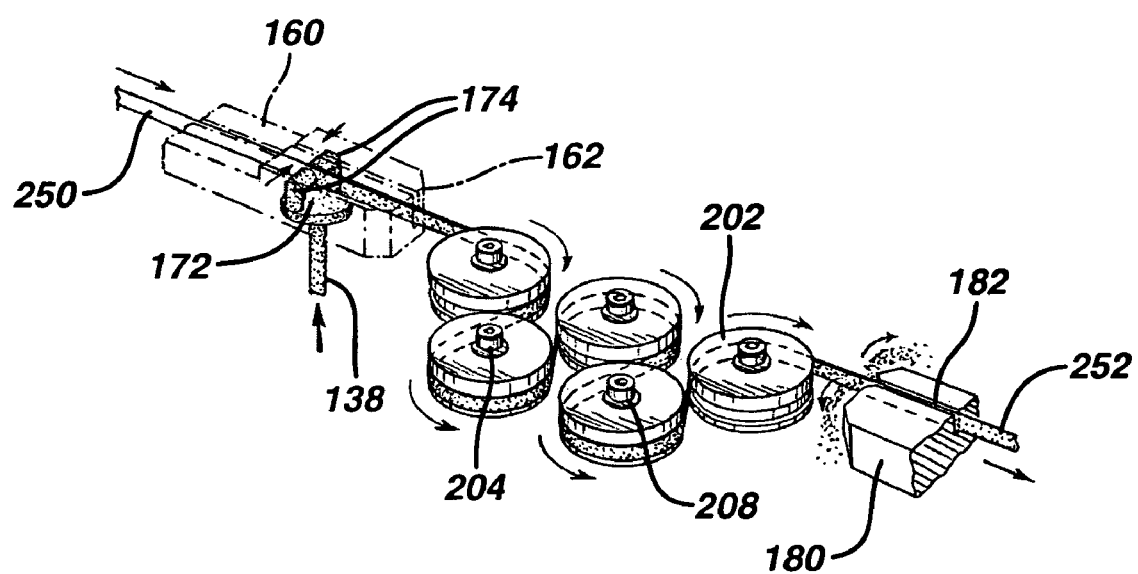
FIG. 5 is a perspective view showing movement of a monofilament tape through entrance and exit blocks and rollers of a roller coating die according to an exemplary embodiment of the present invention.

FIG. 5 is a perspective view showing details of how roller coating die 110 transforms uncoated dental tape 250 to coated dental tape 252. FIG. 5 shows uncoated dental tape 250 proceeding into entrance block 160 at a vertical orientation and travelling along and between the walls (or opposite sides) of entrance block slot 162. Entrance block slot 162 is sized wide enough to produce minimal tension on the vertically oriented, uncoated dental tape 250, but narrow enough that gravity does not cause the lower portion of the uncoated dental tape 250 to receive more coating than the upper portion of the uncoated tape 250. Coating travels vertically through base passage hole 138 to entrance block pool 172, and splits into two coating bores (or passages) 174. In one embodiment, uncoated dental tape 250 is coated simultaneously on both sides as it passes coating bores 174. Coated dental tape 252 then passes around rollers 202 with at least some wrap while maintained in its vertical orientation. Generally, coated dental tape 252 wraps around the rollers at from 90° to 270°. Rollers 202 assist in uniformly applying coating composition to coated dental tape 252. Though FIG. 5 shows five rollers, it is understood that coated dental tape 252 may pass around as few as one roller, or as many as about twenty or more rollers. Downstream of rollers 202 is exit block 180. Coated dental tape 252 proceeds into exit block 180 still vertically oriented and travels along exit block slot 182 which aid in maintaining the vertical orientation of dental tape 252. As mentioned above, the width 182*a* of exit block slot 182 is sized to provide coating composition 5 an additional opportunity to be smoothed onto the surface of coated dental tape 252 and also removes excess coating composition 5 while at the same time minimizing any additional tension caused by movement of dental tape 252 through exit block 180.

Note that all slots discussed above, including cover plate slots (144*a*, 144*b*, 144*c*), base slots (124*a*, 124*b*), entrance block slot 162, and exit block slot 182 may be in the form of a groove having parallel sides or walls, the groove optionally having a radius at its bottom. As will be apparent to those skilled in the art, the dimensions of the groove will depend upon such factors as the denier and type of uncoated dental tape 250 and the amount of coating composition being applied thereto.

Figure 6:
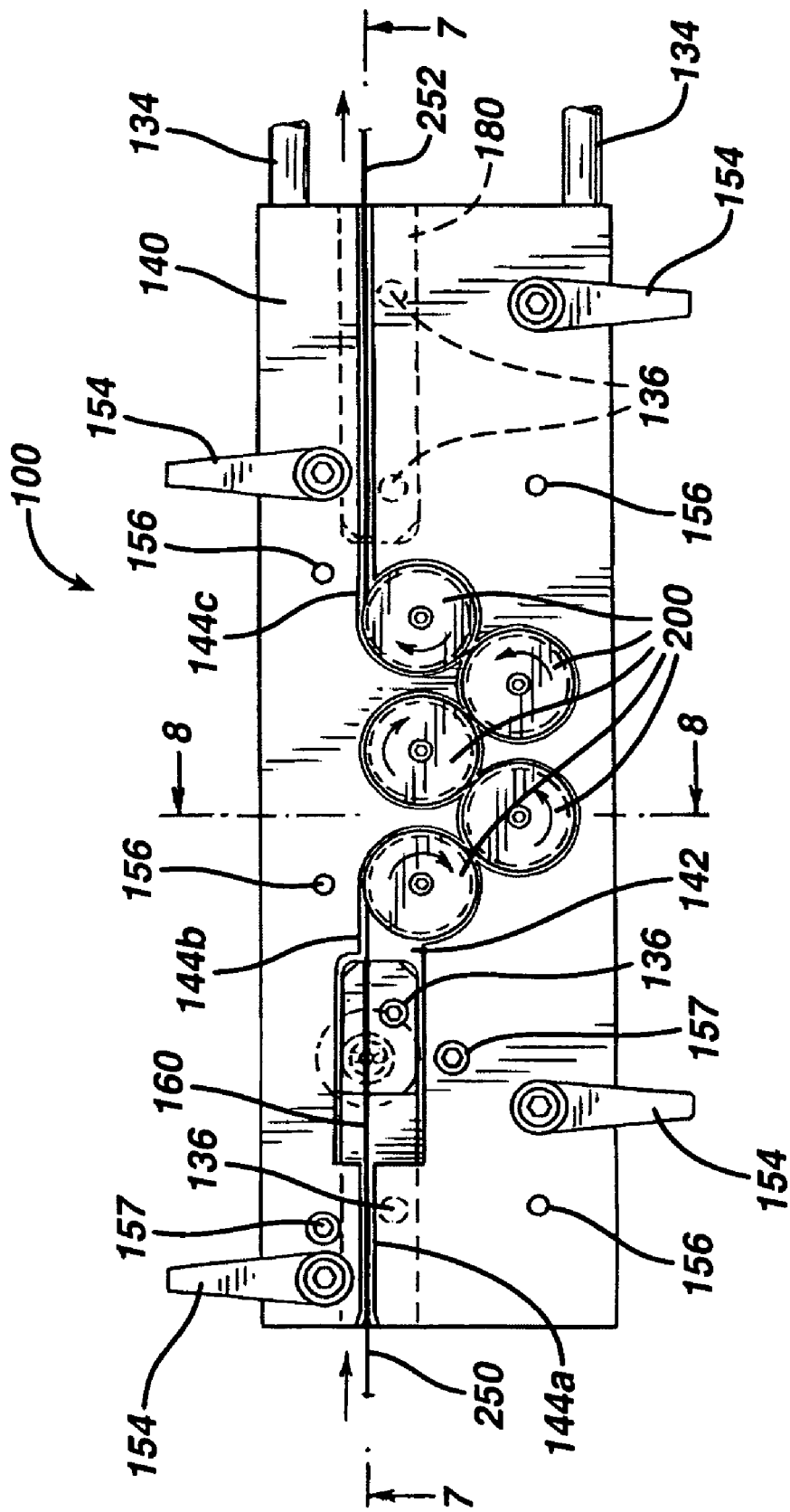
FIG. 6 is a top plan view of a roller coating die according to an exemplary embodiment of the present invention.

FIG. 6 is a top view of an embodiment of coating die 110 showing details of the cover plate 140 and the monofilament coating path. FIG. 6 shows uncoated dental tape 250 proceeding into entrance block 160 where it is coated. Coated dental tape 252 proceeds around roller assemblies 200 to exit block 180 and out of a coating die 110. Entrance block 160 is partially hidden by cover plate 140, but is visible through cover plate window 142. Roller assemblies 200 can be seen through roller wheel windows 146. Exit block 180 is hidden by cover plate 140, but coated dental tape 252 is visible through cover plate slot 144*c*. FIG. 6 also shows threaded handle 154, which are used to hold cover plate 140 to roller die base 120, as well as alignment holes 156 to align cover plate 140 to roller die base 120 prior to attaching the two.

Figure 7:
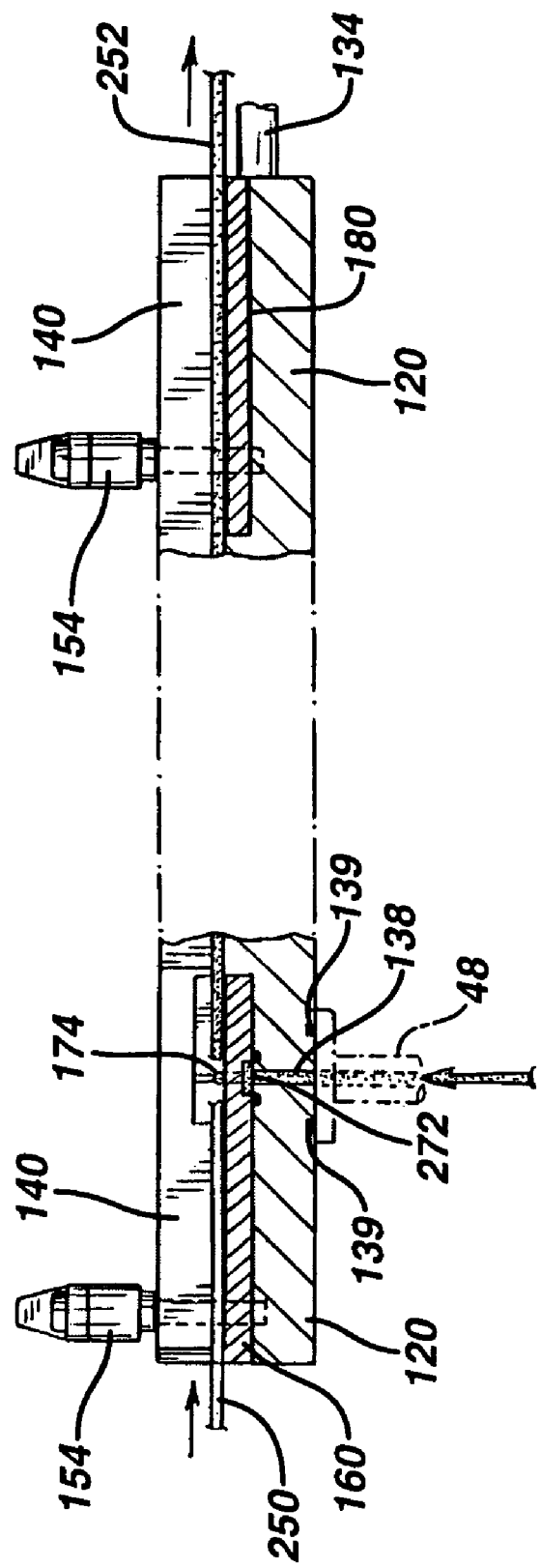
FIG. 7 is a cross-sectional view of a roller coating die according to the exemplary embodiment of FIG. 6 along the plane 7-7.

FIG. 7 is a cross-sectional view of the coat die 110 embodiment of FIG. 6 along plane 7-7. FIG. 7 shows uncoated dental tape 250 proceeding into entrance block 160. Coating travels vertically from second pipe 48 (or coating dispensing pipe receiving coating from displacement pump 46) through base hole 138 to entrance block pool 172, and splits into two coating bores 174 (FIG. 7 shows one of the two bores). In one embodiment, uncoated dental tape 250 is coated simultaneously on both sides as it passes coating bores 174. FIG. 7 also shows coated dental tape 252 travelling through exit block 180 and out of a coating die 110. Threaded handles 154, which are used to hold cover plate 140 to roller die base 120, as well as cartridge heaters 134, which can be used if needed to keep coating composition, in a liquid state, are also shown in the figure.

FIG. 8 is a cross-sectional view of the embodiment of FIG. 6 along plane 8-8. FIG. 8 shows cover plate 140, roller die base 120, cartridge heaters 134, as well as detailed view of roller assembly 200. Roller assembly 200 includes roller 202 which assist in uniformly applying coating composition to coated dental tape 252. In certain embodiments, one end of stub shaft 210 is disposed in center of roller 202, and attached to roller 202 by cap screw 204, flat washer 206, and lock washer 208. The central portion of stub shaft 210 is disposed in inner ring shield bearing 212. The opposing end of stub shaft 210 is disposed in bearing retainer 220, and attached to bearing retainer 220 by cap screw 204, flat washer 206, and lock washer 208. Bearing retainer 220 is attached to roller die base 120 by bearing retainer cap screw 222 and bearing retainer lock washer 224. In one embodiment, three sets of cap screws 222 and lock washers 224 are used to attach bearing retainer 220 to roller die base 120. However, one skilled in the art could use more or less screws to attach the two, or other means of attachment known in the art. Finally, inner ring shield bearing 212 is kept approximately centered in roller assembly recess 126 and roller wheel window 146, by outer race spacer 214.

Figure 9:
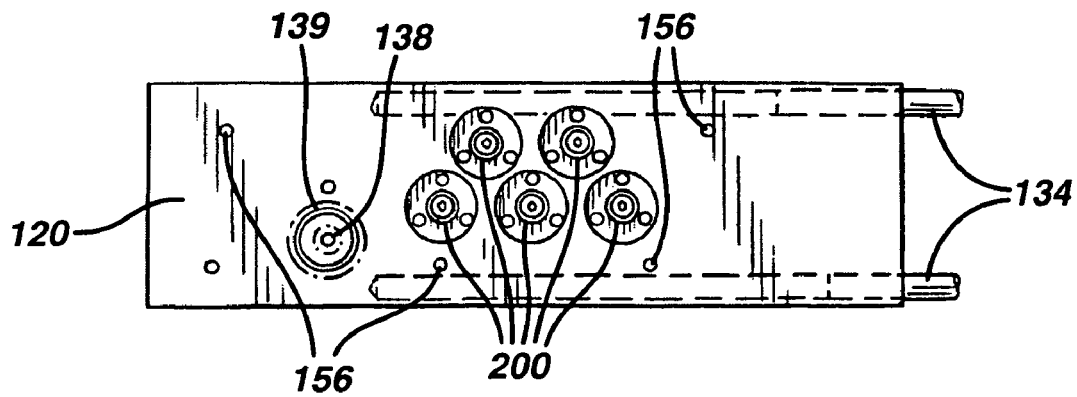
FIG. 9 is a bottom plan view of a coating die according to an exemplary embodiment of the present invention.

FIG. 9 is a bottom view of an embodiment of a roller coating die of the present invention. The FIG. 9 shows five roller assemblies 200, base hole 138, cartridge heaters 134, and alignment holes 156 on roller die base 120. An O-ring 139, is used to prevent leakage of coating composition between positive displacement pump and roller die base 120. Alignment holes 156 are used to align cover plate 140 to roller die base 120 prior to attaching the two.

Figure 10:
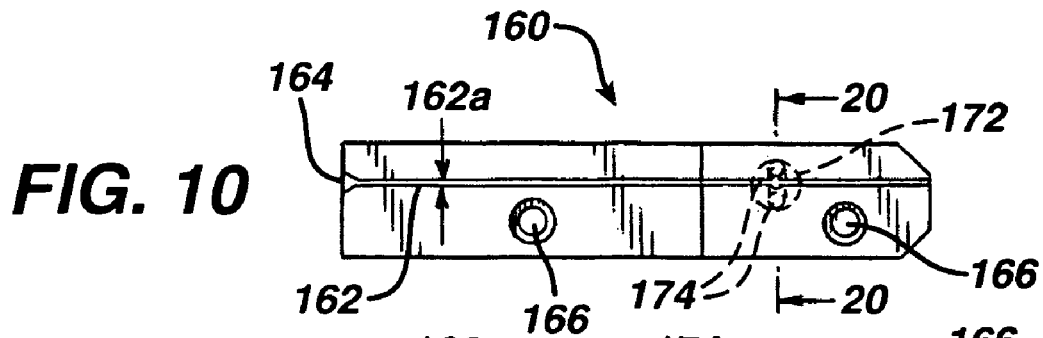
FIG. 10 is a top plan view of an entrance block of a coating die according to an exemplary embodiment of the present invention.
Figure 11:
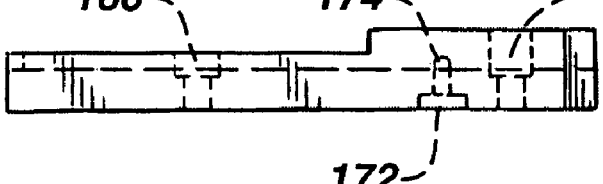
FIG. 11 is a right side elevational view of an entrance block of a coating die according to an exemplary embodiment of the present invention.
Figure 12:
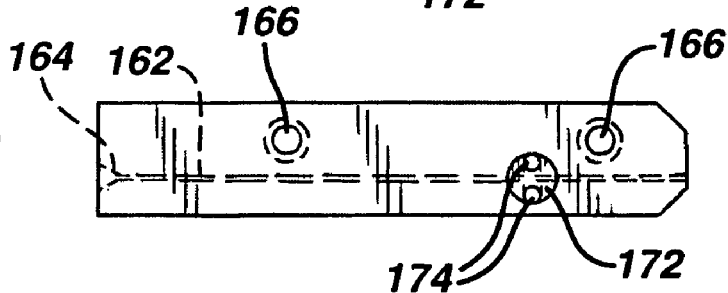
FIG. 12 is a bottom plan view of an entrance block of a coating die according to an exemplary embodiment of the present invention.
Figure 13:
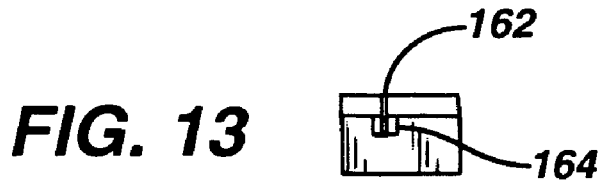
FIG. 13 is a front elevational view of an entrance block of a coating die according to an exemplary embodiment of the present invention.
Figure 14:
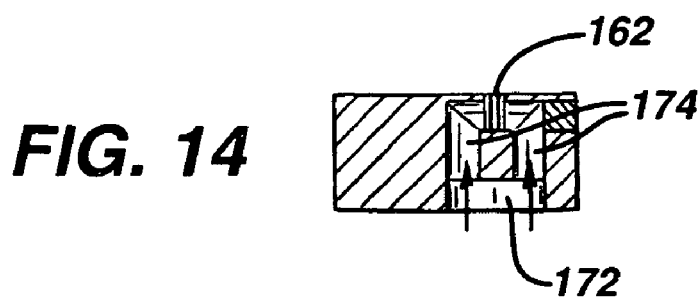
FIG. 14 is a cross-sectional view of an entrance block pool and coating bores of a coating die according to the exemplary embodiment of FIG. 10 along the plane 14-14.

FIGS. 10 through 14 show details of entrance block 160. The FIG. 10 shows entrance block slot 162 and entrance block slot guide 164. Entrance block slot guide 164 is a V-shaped or tapered cut in entrance block 160 to guide uncoated dental tape 250 into entrance block slot 162. The entrance block slot 162 is sized at a width 162*a* such that it maintains the vertical orientation of uncoated dental tape 250 through the entrance block 160, as well as facilitate coating as mentioned above, with little to no additional tension on the dental tape 250. Uncoated dental tape 250 travels along entrance block slot 162 to where it is coated. Coating travels vertically from entrance block pool 172 into two coating bores 174. Uncoated dental tape 250 is coated simultaneously on both sides as it passes coating bores 174. FIGS. 10 to 12 show two optional entrance block holes 166 which may be used to attach entrance block 160 to roller die base 120.

Figure 15:
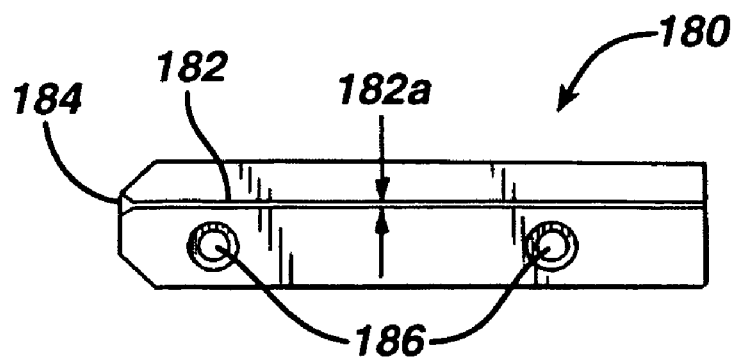
FIG. 15 is a top plan view of an exit block of a coating die according to an exemplary embodiment of the present invention.
Figure 16:
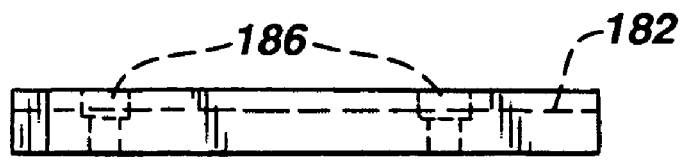
FIG. 16 is a right side elevational view of an exit block of a coating die according to an exemplary embodiment of the present invention.
Figure 17:
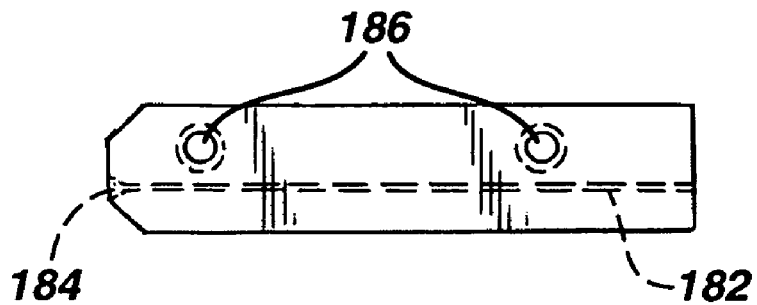
FIG. 17 is a bottom plan view of an exit block of a coating die according to an exemplary embodiment of the present invention.
Figure 18:
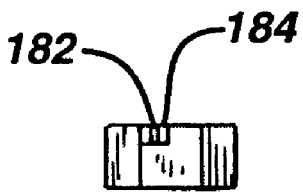
FIG. 18 is a rear elevational view of an exit block of a coating die according to an exemplary embodiment of the present invention.

FIGS. 15 through 18 show details of exit block 180. FIG. 15 shows exit block slot 182 and entrance block slot guide 184. Entrance block slot guide 184 is a V-shaped cut in exit block 180 to guide coated dental tape 252 into exit block slot 182. Exit block slot 182 allows coating composition an additional opportunity to be smoothed onto the surface of coated dental tape 252. The width 182*a* of exit block slot 182 is sized to provide coating composition 5 an additional opportunity to be smoothed onto the surface of coated dental tape 252 and also removes excess coating composition 5 while at the same time minimizing any additional tension caused by movement of dental tape 252 through exit block 180. Coated dental tape 252 travels along exit block slot 182 until it leaves roller coating die 110. FIGS. 15 to 17 show two optional exit block holes 186 which may be used to attach exit block 180 to roller die base 120.

While illustrated as separate components, it will be readily understood by the skilled artisan that entrance block 160 and exit block 180 (along with their distinct structural characteristics) can be integral with roller die base 120 and/or cover plate 140 without changing the performance or function of coating die 110. Maintaining entrance block 160 and exit block 180 as separate components however, provides the convenience of interchangeability. For example, separate entrance block 160 and exit block 180 components allow for the interchange of entrance block 160 and/or exit block 180 with entrance and exit blocks of differing slot (162, 182) and slot guide (164 and 184) widths.

Coating composition 5 once applied to dental tape 10 must be solidified. Solidification can be accomplished by having a cooling area 60. Cooling area 60 can be an open area where coating 5 cools under ambient conditions. Alternatively, cooling area 60 can be a chamber where refrigerated or room air is blown over dental tape 10 to increase the rate of cooling. In order to avoid undesirable discontinuities in coating 5, dental tape 10 should not contact any surfaces until coating 5 has solidified.

Once coating 5 is cooled sufficiently to prevent any disruption of the outer surface, it is rewound on floss rewinding system 70. Rewinding system 70, shown in FIG. 2, has take-up spool 72 and speed sensing roll 74 as described before, as well as a drive motor 80, a series of timing belts (all labeled 84) and timing belt pulleys (all labeled 82), and a traversing cam guide 76 disposed on a traverse barrel cam 86. For 6 pound rolls or less, optionally 5 pounds or less, or optionally 4 pounds of less of dental tape rolled onto spool 72, the tension of the dental tape 10 is monitored using conventional tension measuring devices (such as Checkline, supplied by Electromatic Equipment Co., Cedarhurst, N.Y.) prior to rewinding and the speed adjusted accordingly such that the tension of the dental tape 10 during rewinding process is less than 300 (or about 300) grams-force, optionally less than 250, (or about 250) grams-force or optionally from about 190 grams-force to about 200 grams-force. Traversing cam guide 76 and traverse barrel cam 86 are disposed in a traversing cam guide housing 78 which has a traversing cam guide housing slot 79.

Figure 2:
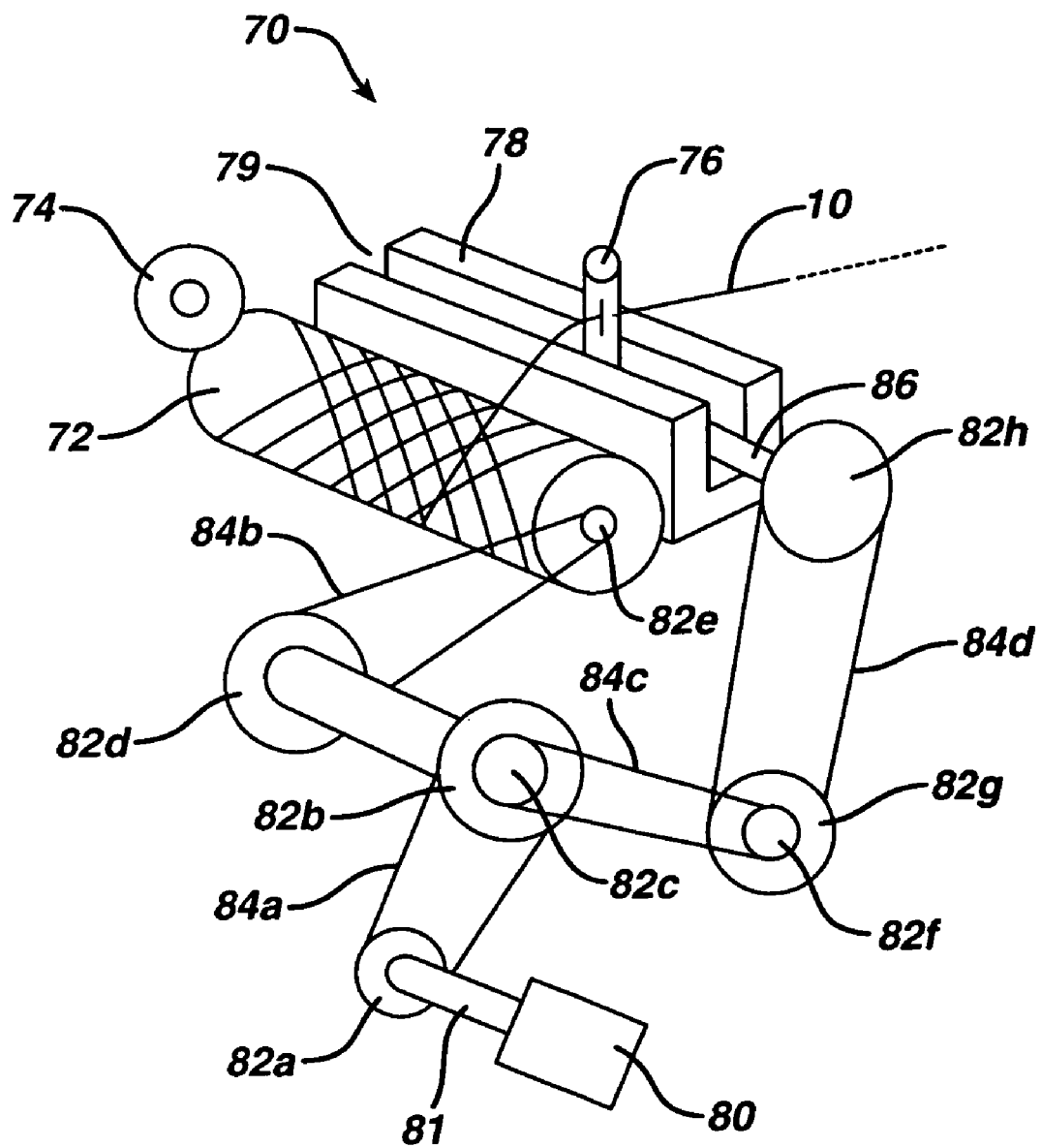
FIG. 2 is a schematic illustration of one embodiment of the rewind mechanism of the present invention.
Figure 19:
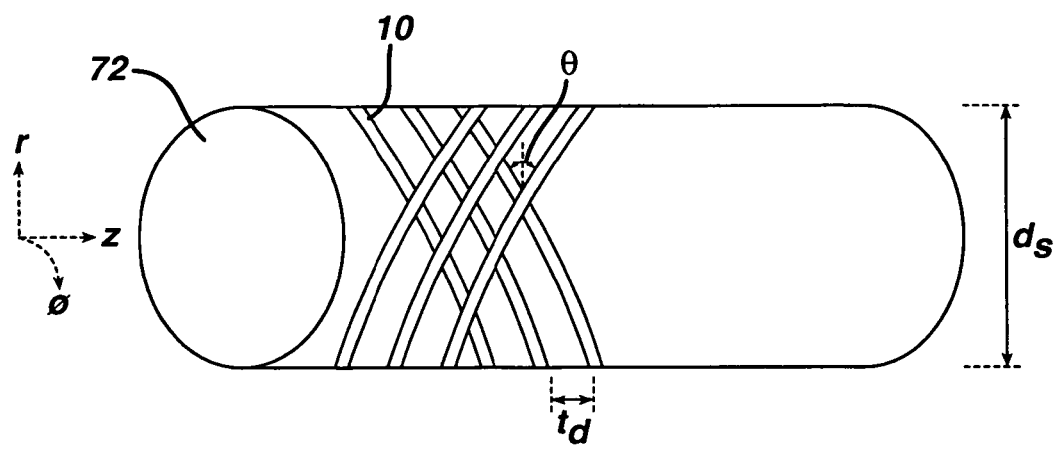
FIG. 19 is a 3 dimensional schematic illustration of one embodiment of coated roll of dental tape showing the helix angle θ formed by the strands of dental tape and the plane rΦ perpendicular to the spool's longitudinal axis z.

Rewinding system 70 is a traversing rewinder in that as take-up spool 72 rotates, traversing cam guide 76 is traversed back and forth along its length (see FIG. 2). The take-up spool 72 has a longitudinal axis z; a plane rΦ which is perpendicular to longitudinal axis z. and a circumference C (equal to the product of the spool core diameter $d_s$ and π) as shown in FIG. 19. Rewinding system 70 functions as follows: spindle 81 of motor 80 rotates to drive timing belt pulley 82a, which, through timing belt 84a, drives timing belt pulleys 82b and 82c. Timing belt pulley 82b drives timing belt pulley 82d, which, in turn, drives timing belt pulley 82e via timing belt 84b. Timing belt pulley 82e is disposed on the end of take-up spool 72, so as it rotates, take-up spool 72 rotates. Timing belt pulley 82c, via timing belt 84c, drives timing belt pulleys 82f and 82g. Timing belt pulley 82g drives timing belt pulley 82h via timing belt 84d. Timing belt pulley 82h is disposed on the end of traverse barrel cam 86, so as pulley 82h rotates, traverse barrel cam 86 rotates. Traversing cam guide 76 is disposed on traverse barrel cam 86 such that when traverse barrel cam 86 rotates, traversing cam guide 76 traverses back and forth along its length. Suitable traversing rewinders can be readily built or purchased from companies such as Leesona Corporation.

Figure 20:
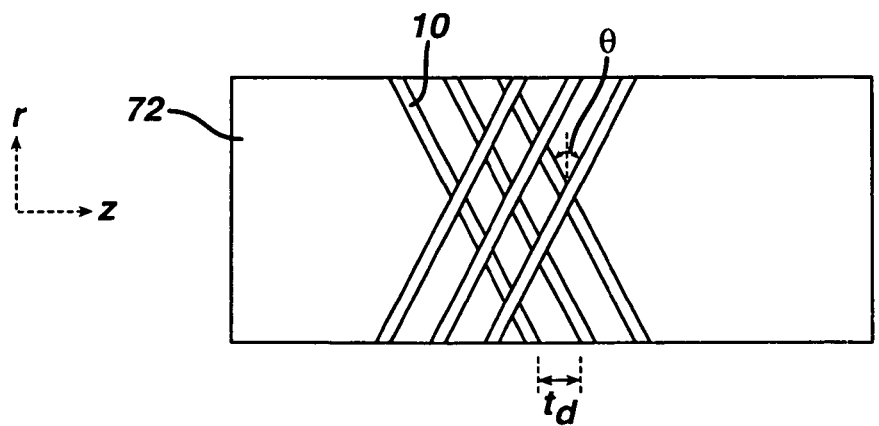
FIG. 20 is a 2 dimensional schematic illustration of one embodiment of coated roll of dental tape showing the helix angle θ formed by the strands of dental tape and side r of plane rΦ and the spacing between the individual strands of dental tape in each layer of dental tape.

In certain embodiments, the pulley sizes and traverse barrel cam are selected for the rewinding system as described below:
a.) the pulleys are selected (or adjusted) such that the product of the pulley ratios or Ratio A (which determines the traversing movement of traversing cam guide (inches) per revolution of Spool 72 (inches)) is as follows:

Ratio $A = P_1/P_2 \times P_3/P_4 \times P_{Z-1}/P_Z$

Where $P_1$ through $P_Z$ are the pulley sizes of the sequentially ordered pulleys from the pulley rotating the take-up spool 72 or $P_1$ to the pulley rotating traverse barrel cam 86 or $P_Z$ used in association with b.) the traverse barrel cam 86, which is selected such that the product of the cam advance (or, total length [end to end] traversed by traversing cam guide 76 divided by the turns of the traverse barrel cam 86 needed to achieve the total traverse of traversing cam guide 76) and Ratio A when divided by the circumference C of the core of take-up spool 72 (i.e., take-up spool 72 without tape 10) produces a Ratio B, where Ratio $B = $(cam advance×Ratio $A$)/Circumference $C$ and where Ratio B provides a helix angle θ of from about 3.5 degrees to about 5 degrees, where the helix angle θ is formed by a strand of dental tape and plane rΦ of the spool 72 which is perpendicular to the longitudinal axis z of the spool 72 as shown in FIGS. 19 and 20 and is determined by formula:

$\sin^{-1}$(Helix Angle θ)=Ratio $B$

Without being limited by theory, it is believed that obtaining a helix angle θ of about 3.5 degrees to about 5.5 degrees provides take-up spool rolls 72 of dental tape 10 such that:
  i) in any given layer of the dental tape, the strands of dental tape 10 forming that layer do not overlap, or, optionally, do not touch or, optionally, have a space there between $t_s$ of up to 1/32 (or about 1/32) of an inch and
  ii.) the strands of dental tape 10 forming each layer of dental tape 10 overlap with the strands of dental tape 10 forming the preceding layer of dental tape 10 to form intersection angles of about 7 to about 11 degrees (or twice the helix angle θ)

If it is desired to apply a second coating to dental tape 10, this may be done by locating another coating line and cooling chamber downstream of cooling area 60.

In certain embodiments, spool 72 dental tape 10 is then removed for later processing into bobbins 90. Bobbins of tape as shown in FIGS. 22a and 22b are formed from dental tape 10 unwound from spool 72 onto bobbin spool cores 92 of selected width $w_c$ as shown in FIG. 21 and packaged into dispensers 95 of selected width $w_d$ for use by consumers as shown in FIGS. 23a and 23b. In certain embodiments, the bobbin spool cores 92 have an aspect ratio of greater than about 2:1, optionally about 3:1, where the aspect ratio is the ratio of bobbin spool diameter to width. The dental tape 10 winds from spool 72 onto the bobbin spool cores 92 to form tape bobbins where the wound tape widths $w_b$ such that wound tape width $w_b$ exceeds the width of the bobbin spool core $w_c$ by no more that 10% (or about 10%), optionally, 5% (or about 5%), optionally 2.5% (or about 2.5%), optionally 1% (or about 1%). Hence, the inventive rewinding system 70 which produces helix angles θ of from about 3.5 degrees to about 5.5 degrees ensures that the wound tape widths $w_b$ of the finished tape bobbins formed from spool 72 do not telescope so as to interfere with the packaging of the finished tape bobbin into dispensers 95 specifically designed to movably accommodate bobbin spool cores 92 of widths $w_c$. More generally, the inventive rewinding system 70 permits the use of narrower width dispensers particularly in cases where the tape or floss is made of an elastomeric material.

Several examples of the present invention are set forth below to further illustrate the nature of the invention and the manner of carrying it out. However, the invention should not be considered as being limited to the details thereof.

In the following Examples, the mentioned percentages are weight percentages.

EXAMPLE 1

Dental tape spool rolls were formed in accordance with the coating and winding processes of the present invention and using the component sizes and/or type described below and summarized in Table I.

TABLE I

| Component | Type/Size |
|---|---|
| Pulley 82e | 14 Teeth |
| Pulley 82d | 17 Teeth |
| Pulley 82c | 19 Teeth |
| Pulley 82f | 14 Teeth |

TABLE I-continued

| Component | Type/Size |
|---|---|
| Pulley 82g | 16 Teeth |
| Pulley 82h | 20 Teeth |
| Traversing Cam | 11.5 inches, 6 turns end to end cam |
| Guide Traverse | |

Ordering the above pulley sizes sequentially (e.g., 82e is connected to 82d which is connected 82c etc. as shown in FIG. 2) and determining the product of the ratios of the sizes of the sequentially ordered pulleys or Ratio A (as shown in I below)

$$\text{Ratio } A = P_1/P_2 \times P_3/P_4 \times P_{Z-1}/P_Z \quad \text{I}$$

Where $P_1$ to $P_Z$ are the sizes of the pulleys sequentially ordered from spool 72 and to the traverse barrel cam 86 of rewinding system 70, results in the following ratio:

$$\text{Ratio } A = (\text{Pulley } 82e / \text{Pulley } 82d) \times (\text{Pulley } 82c / \text{Pulley } 82f) \times$$
$$(\text{Pulley } 82g / \text{Pulley } 82h)$$
$$= (14/17) \times (19/14) \times (16/20)$$
$$= 0.8941$$

A traverse barrel cam was selected to provide a traversing cam guide traverse of 11.5 inches end to end for every 6 revolutions of spool 72. This results in a cam advance equal to the following:

$$\text{Cam Advance} = \frac{\text{Cam Guide Traverse}}{6 \text{ Revolutions of Traverse Barrel Cam}}$$
$$= 11.5/6$$
$$= 1.9166 \text{ inches per Traverse Barrel Cam revolution}$$

Ratio A indicates that for each revolution of the spool 72, the traverse barrel cam 86 travels 0.8941 of the spool revolution. This results in the following travel distance for the traversing cam guide 76 per revolution of spool 72:

Travel Distance of traversing cam guide per revolution of spool =

$$\text{Cam Pulley Ratio} \times \text{Cam Advance} =$$
$$0.8941 \times 1.9166 = 1.71 \text{ inches per spool revolution}$$

The core diameter $d_s$ of spool 72 was measured to be 6.21 inches, therefore, the distance traveled by any point on the outer surface of the core of spool 72 after one revolution of spool 72 or circumference C can be calculated as follows:

Circumference $C = 6.21$ inches$\times \pi = (6.21)3.1411 = 19.5$ inches

The helix angle θ (the angle formed by a strand of dental tape and plane rΦ of the spool which is perpendicular to the longitudinal axis z of the spool as shown in FIG. 19) formed by dental tape 10 as it is initially wound around the core of spool 72 can then be calculated as follows:

Travel Distance of traversing cam guide per spool revolution/Circumference $C = 1.71/19.5$ $1.71/19.5 = 0.0876 = \sin^{-1} θ$ (Helix Angle)

Where Helix Angle θ=5.03°

As will be understood by the skilled artisan, as the spool 72 roll grows, the helix angle decreases. For example, as one inch of dental tape is wound onto the core of spool 72, helix angle θ decreases. This is exemplified as follows:

The diameter of spool after adding one inch layer of tape=6.21 inches+2 inches (1 inch added layer results in diameter increasing by 2 inches)=8.21 inches, hence:

Circumference of Spool with Tape=diameter of spool with tape$\times \pi = (8.21)3.1411 = 25.7$ inches Travel distance of traversing cam guide per spool revolution/Circumference of Spool with Tape=$1.71/25.7$ inches=$0.066 = \sin^{-1} θ'$ (Helix Angle)

Where Helix Angle θ'=3.8°

Hence, as about an inch of material is wound around the spool, the helix angle chances by about 1° (θ−θ'=5.03°−3.8°=1.5°).

Using the above traverse barrel cam and pulley sizes, Rolls 1-7 (representative of spool 72 in FIG. 1) were formed and, then, Rolls 1-7 were subsequently used to form separate tape bobbins (representative bobbins formed on bobbin spool 90 in FIG. 1). The parameters of the formed rolls and coating and rewinding process are summarized in Tables II and III.

TABLE II (Wax Coating Formulation)

| Ingredient | Amount (%) |
|---|---|
| Microcrystaline Wax[1] | 82% |
| Flavor | 17% |
| Sodium Saccharin | 1% |

[1]Multiwax-W445, supplied by Crompton Corp. Petrolia, Pa

TABLE III

| Process Parameters | Roll 1 | Roll 2 | Roll 3 | Roll 4 | Roll 5 | Roll 6 | Roll 7 |
|---|---|---|---|---|---|---|---|
| Line Speed (feet per min.) | 1600 | 1600 | 1600 | 1600 | 1600 | 1600 | 1600 |
| Tape Tension prior to rewinding on rolls (grams-force) | 190 | 190 | 200 | 205 | 205 | 200 | 210 |
| Tank Temp ° F. | 200 | 200 | 200 | 200 | 200 | 200 | 200 |
| Die Temp ° F. | 200 | 200 | 200 | 200 | 200 | 200 | 200 |

TABLE III-continued

| Process Parameters | Roll 1 | Roll 2 | Roll 3 | Roll 4 | Roll 5 | Roll 6 | Roll 7 |
|---|---|---|---|---|---|---|---|
| Tape (yarn) Start Wt (grams). | 3738 | 2907 | 3994 | 2998 | 2257 | 3804 | 2977 |
| Tape (yarn) Finish Wt (grams). | 2907 | 2079 | 2998 | 2257 | 1364 | 2977 | 2131 |
| Tape (yarn) Wt. (grams) | 831 | 828 | 996 | 741 | 893 | 827 | 846 |
| Coated Tape and Core (grams) | 2578 | 2661 | 2704 | 2637 | 2654 | 2704 | 2630 |
| Core Tare (grams) | 1398 | 1462 | 1309 | 1367 | 1357 | 1474 | 1370 |
| Coated Tape Wt. (grams) | 1180 | 1199 | 1395 | 1270 | 1297 | 1230 | 1260 |
| Wax Added[1] (grams) | 349 | 371 | 409 | 329 | 406 | 403 | 414 |
| Wax Add-on %[2] | 29.5 | 31.3 | 306 | 30.7 | 31.2 | 32.7 | 32.8 |
| Wt. Roll[3] (lbs.) t | 2.60 | 2.65 | 2.94 | 2.35 | 2.86 | 2.71 | 2.77 |

[1]Wax Added = Tape Wt. − Coated Tape Wt.
[2]Wax Add-on % = (Waxed Added/Coated Tape Wt.) (100)
[3]Wt. Roll = Coated Tape Wt./454 grams/lb.

The bobbins produced on bobbin spools of width 10.3 mm and percent of bobbins rejected as exhibiting unsatisfactory telescoping are summarized in Table IV.

TABLE IV

| # Bobbin Produced | 236 | 240 | 261 | 213 | 259 | 296 | 251 |
|---|---|---|---|---|---|---|---|
| # Rejects[1] | 0 | 0 | 0 | 8 | 1 | 0 | 0 |

[1]Rejected bobbins rolls are bobbin rolls in which the width of the wound tape on bobbin exceeded the bobbin dispenser width of 11.2 mm.
Total Bobbins Produced = 1711
Total Rejects = 9
% Rejects = 0.5%

EXAMPLE 2

Dental tape spool rolls are formed in accordance with the coating and winding processes of the present invention and using the component sizes and/or type described below and summarized in Table V.

TABLE V

| Component | Type/Size |
|---|---|
| Pulley $P_1$ | 14 Teeth |
| Pulley $P_2$ | 14 Teeth |
| Pulley $P_3$ | 15 Teeth |
| Pulley $P_4$ | 19 Teeth |
| Pulley $P_5$ | 17 Teeth |
| Pulley $P_6$ | 20 Teeth |
| Traversing Cam Guide Traverse | 12 inches, 6 turns end to end cam |

The above pulley sizes should be ordered sequentially (as illustrated FIG. 2, where 82e (which would be $P_1$) is connected to 82d (which would be $P_2$) which is connected 82c (which would be $P_3$) etc.). The product of the ratios of the sizes of the sequentially ordered pulleys or Ratio A can be determined as shown in I below:

$$\text{Ratio } A = P_1/P_2 \times P_3/P_4 \times P_{Z-1}/P_Z \quad \text{I}$$

Using the size values from Table results in the following Ratio A:

$$\text{Ratio } A = P_1/P_2 \times P_3/P_4 \times P_5/P_6 = (14/14) \times (15/19) \times (17/20) = 0.671$$

A traverse barrel cam can be selected to provide a traversing cam guide traverse of 12 inches end to end for every 6 revolutions of traverse barrel cam 86. This results in a cam advance equal to the following:

$$\text{Cam Advance} = \frac{\text{Traversing Cam Guide Traverse}}{6 \text{ Revolutions of Traverse Barrel Cam}}$$

$$= 12/6$$

$$= 2 \text{ inches per Traverse Barrel Cam revolution}$$

Ratio A indicates that for each revolution of the spool 72, the traverse barrel cam 86 travels 0.671 of the spool revolution. This results in the following travel distance for the traversing cam guide 76 per revolution of spool 72:

Travel Distance of traversing cam guide per revolution of spool =

Cam Pulley Ratio × Cam Advance =

$0.671 \times 2 = 1.342$ inches per spool revolution

A core diameter $d_s$ of spool 72 of 5 inches can be selected such that the distance traveled by any point on the outer surface of the core of spool 72 after one revolution of spool 72 or circumference C can be calculated as follows:

Circumference $C = 5$ inches $\times \pi = (5)3.14 = 15.7$ inches

The helix angle θ (the angle formed by a strand of dental tape and plane rφ of the spool which is perpendicular to the longitudinal axis z of the spool as shown in FIG. 19) which forms by dental tape 10 as it is initially wound around the core of spool 72 can then be calculated as follows:

Travel Distance of traversing cam guide per spool revolution/Circumference $C = 1.342/15.7$ $1.342/15.7 = 0.0854 = \sin^{-1} \theta$ (Helix Angle)

Where Helix Angle θ=4.9°

As one inch of dental tape is wound onto the core of spool 72, helix angle θ decreases. This can be calculated as follows: The diameter of spool after 1 adding one inch layer of tape=5 inches+2 inches (1 inch added layer results in diameter increasing by 2 inches)=7 inches, hence:

Circumference of Spool with Tape=diameter of spool with tape×π=(7)3.14=21.98 inches Travel distance of traversing cam guide per spool revolution/Circumference of Spool with Tape=1.342/21.98 inches=0.061=sin−1 θ' (Helix Angle)

Where Helix Angle θ'=3.5°

Therefore, as about an inch of material is wound around the spool, the helix angle chances by about 1° (θ−θ′=4.9°−3.5°=1.4°).

Using the above traverse barrel cam and pulley sizes, rolls (representative of spool 72 in FIG. 1) can be formed, which rolls can subsequently be used to form separate tape bobbins. (representative bobbins formed on bobbin spool 90 in FIG. 1).

EXAMPLE 3

Dental tape spool rolls are formed in accordance with the coating and winding processes of the present invention and using the component sizes and/or type described below and summarized in Table VI.

TABLE VI

| Component | Type/Size |
|---|---|
| Pulley $P_1$ | 14 Teeth |
| Pulley $P_2$ | 14 Teeth |
| Pulley $P_3$ | 14 Teeth |
| Pulley $P_4$ | 14 Teeth |
| Pulley $P_5$ | 16 Teeth |
| Pulley $P_6$ | 20 Teeth |
| Traversing Cam Guide Traverse | 12 inches, 5 turns end to end cam |

The above pulley sizes should be ordered sequentially (as illustrated FIG. 2, where 82e (which would be $P_1$) is connected to 82d (which would be $P_2$) which is connected 82c (which would be $P_3$) etc.). The product of the ratios of the sizes of the sequentially ordered pulleys or Ratio A can be determined as shown in I below:

$$\text{Ratio } A = P_1/P_2 \times P_3/P_4 \times P_{Z-1}/P_Z \qquad \text{I}$$

Using the size values from Table results in the following Ratio A:

$$\text{Ratio } A = P_1/P_2 \times P_3/P_4 \times P_5/P_6 = (14/14) \times (14/14) \times (16/20) = 0.80$$

A traverse barrel cam can be selected to provide a traversing cam guide traverse of 12 inches end to end for every 5 revolutions of traverse barrel cam 86. This results in a cam advance equal to the following:

$$\text{Cam Advance} = \frac{\text{Traversing Cam Guide Traverse}}{5 \text{ Revolutions of Traverse Barrel Cam}}$$

$$= 12/5$$

$$= 2.4 \text{ inches per Traverse Barrel Cam revolution}$$

Ratio A indicates that for each revolution of the spool 72, the traverse barrel cam 86 travels 0.80 of the spool revolution. This results in the following travel distance for the traversing cam guide 76 per revolution of spool 72:

$$\text{Travel Distance of traversing cam guide per revolution of spool} =$$

$$\text{Cam Pulley Ratio} \times \text{Cam Advance} =$$

$$0.80 \times 2.4 = 1.92 \text{ inches per spool revolution}$$

A core diameter $d_s$ of spool 72 of 7 inches can be selected such that the distance traveled by any point on the outer surface of the core of spool 72 after one revolution of spool 72 or circumference C can be calculated as follows:

$$\text{Circumference } C = 5 \text{ inches} \times \pi = (7)3.14 = 21.98 \text{ inches}$$

The helix angle θ (the angle formed by a strand of dental tape and plane of the spool rφ which is perpendicular to the longitudinal axis of the spool as shown in FIG. 19) which forms by dental tape 10 as it is initially wound around the core of spool 72 can then be calculated as follows:

$$\text{Travel Distance of traversing cam guide per spool revolution/Circumference } C = 1.92/21.98$$

$$1.92/21.98 = 0.0873 = \sin^{-1} \theta \text{ (Helix Angle)}$$

Where Helix Angle θ=5.01°

As one inch of dental tape is wound onto the core of spool 72, helix angle θ decreases. This can be calculated as follows:

The diameter of spool after 1 adding one inch layer of tape=7 inches+2 inches (1 inch added layer results in diameter increasing by 2 inches)=9 inches $$\text{Circumference of Spool with Tape} = \text{diameter of spool with tape} \times \pi = (9)3.14 = 28.26 \text{ inches}$$

Travel distance of traversing cam guide per spool revolution/Circumference of Spool with Tape=1.92/28.26 inches=0.068=sin−1 θ′ (Helix Angle)

Where Helix Angle θ′=3.9°

Therefore, as about an inch of material is wound around the spool, the helix angle chances by about 1° (θ−θ′=5.01°−3.9°=1.11°).

Using the above traverse barrel cam and pulley sizes, rolls (representative of spool 72 in FIG. 1) can be formed, which rolls can subsequently be used to form separate tape bobbins (representative bobbins formed on bobbin spool 90 in FIG. 1).

What is claimed is:

1. A bobbin of elastomeric tape, comprising:
   a. a spool having a width; and
   b. an elastomeric yarn strand wound onto the spool to form combined yarn strands on the spool having width $W_b$, wherein each yarn strand has a width smaller than $W_b$, wherein the percent at which the width formed by the elastomeric yarn exceeds the width of the spool by no more than 10 percent of the width of the spool.

2. The bobbin of claim 1, wherein the percent at which width formed by the elastomeric yarn exceeds the width of the spool by no more than 7.5 percent of the width of the spool.

3. The bobbin of claim 2, wherein the percent at which width formed by the elastomeric yarn exceeds the width of the spool by no more than 5 percent of the width of the spool.

4. The bobbin of claim 1, wherein the spool has an aspect ratio greater than about 2:1.

5. The bobbin of claim 4, wherein the aspect ratio of the spool is greater than about 3:1.

6. A dental tape dispenser comprising
   a. a housing;
   b. a bobbin movably connected within the housing, the bobbin comprising:
      i. a spool having a width; and
      ii. an elastomeric yarn strand wound onto the spool to form combined yarn strands on the spool having a width $W_b$, wherein each yarn strand has a width smaller than $W_b$, wherein the percent at the which width formed by the elastomeric yarn exceeds the width of the spool by no more than 10 percent of the width of the spool.

* * * * *

UNITED STATES PATENT AND TRADEMARK OFFICE
CERTIFICATE OF CORRECTION

| | | |
|---|---|---|
| PATENT NO. | : 8,316,865 B2 | Page 1 of 1 |
| APPLICATION NO. | : 12/185354 | |
| DATED | : November 27, 2012 | |
| INVENTOR(S) | : Ochs et al. | |

It is certified that error appears in the above-identified patent and that said Letters Patent is hereby corrected as shown below:

Column 3, lines 40 to 43, the term "by" between the phrases "the percent at which the width formed by the elastomeric yarn exceeds the width of the spool" and "no more than 10 percent of the width of the spool" should read --is--.

Column 3, lines 52 to 54, the term "by" between the phrases "the percent at which the width formed by the elastomeric yarn exceeds the width of the spool" and "no more than 10 percent of the width of the spool" should read --is--.

Column 20, lines 41 to 43, the term "by" between the phrases "the percent at which the width formed by the elastomeric yarn exceeds the width of the spool" and "no more than 10 percent of the width of the spool" should read --is--.

Column 20, lines 44 to 46, the term "by" between the phrases "the percent at which width formed by the elastomeric yarn exceeds the width of the spool" and "no more than 7.5 percent of the width of the spool" should read --is--.

Column 20, line 45, before the phrase "width formed by the elastomeric yarn", please insert --the--.

Column 20, lines 47 to 49, the term "by" between the phrases "the percent at which width formed by the elastomeric yarn exceeds the width of the spool" and "no more than 5 percent of the width of the spool" should read --is--.

Column 20, line 48, before the phrase "width formed by the elastomeric yarn", please insert --the--.

Column 20, lines 62 to 64, the term "by" between the phrases "the percent at which width formed by the elastomeric yarn exceeds the width of the spool" and "no more than 10 percent of the width of the spool" should read --is--.

Column 20, line 62, before the phrase "width formed by the elastomeric yarn", please insert --the--.

Signed and Sealed this
Twelfth Day of March, 2013

Teresa Stanek Rea
*Acting Director of the United States Patent and Trademark Office*